United States Patent [19]

Bernhard et al.

[11] Patent Number: 4,585,885
[45] Date of Patent: Apr. 29, 1986

[54] CYCLOHEXENONE DERIVATIVES AND PROCESS FOR MAKING SAME

[75] Inventors: Kurt Bernhard, Lupsingen; Robert K. Müller, Basel; Robert Spruijtenburg, Reinach, all of Switzerland

[73] Assignee: Hoffmann-La Roche Inc., Nutley, N.J.

[21] Appl. No.: 524,541

[22] Filed: Aug. 19, 1983

[30] Foreign Application Priority Data

Aug. 20, 1982 [CH] Switzerland .................. 4983/82
Jun. 21, 1983 [CH] Switzerland .................. 3392/83

[51] Int. Cl.⁴ .................. C07F 7/04; C07F 7/08; C07F 7/18
[52] U.S. Cl. .................. 556/436; 556/443; 556/444; 556/446; 556/449; 556/482
[58] Field of Search .............. 556/436, 443, 444, 446, 556/449, 482

[56] References Cited

U.S. PATENT DOCUMENTS 4,210,596  7/1980  Cella ................................. 556/436
4,238,401 12/1980  Cella et al. .......................... 556/436
4,245,109  1/1981  Mayer et al. ........................ 560/61

Primary Examiner—Paul F. Shaver
Attorney, Agent, or Firm—Jon S. Saxe; George M. Gould; William H. Epstein

[57] ABSTRACT

A silyl-enol ether of the formula

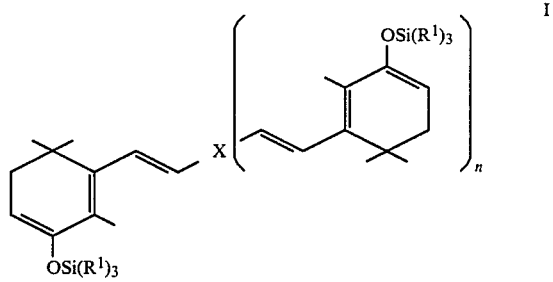

wherein n stands for the number and X stands for a group

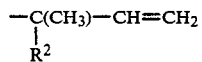

or n stands for the number 1 and X stands for the 6,11-dimethylhexadeca-2,4,6,8,10,12,14-heptaene-2,15-diyl group, the symbols $R^1$ have the same or different significances and denote alkyl groups, and the symbol $R^2$ represents a trialkylsiloxy group $-OSi(R^1)_3$ or an ether group, is oxidized with percarboxylic acid and, if desired, the resulting α-siloxy ketone is hydrolyzed to an α-hydroxy ketone. This process is especially suitable for the manufacture of astaxanthin.

2 Claims, No Drawings

CYCLOHEXENONE DERIVATIVES AND PROCESS FOR MAKING SAME

The present invention is concerned with a novel process for the manufacture of cyclohexenone derivatives, namely of astaxanthin and intermediates in the synthesis of astaxanthin. The invention is also concerned with novel intermediates in this process.

The process provided by the invention comprises oxidizing silyl-enol ether of the general formula

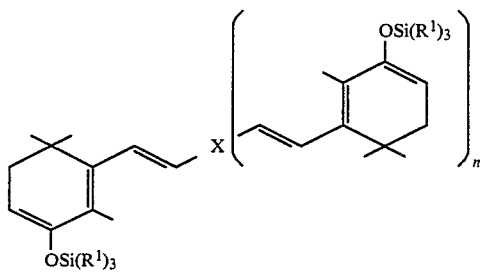

wherein n stands for the number 0 and X stands for a group

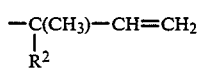

or n stands for the number 1 and X stands for the 6,11-dimethylhexadeca-2,4,6,8,10,12,14-heptaene-2,15-diyl group, the symbols $R^1$ have the same or different significances and denote alkyl groups, and the symbol $R^2$ represents a trialkylsiloxy group $-OSi(R^1)_3$ or an ether group, with a percarboxylic acid and, if desired, hydrolyzing the resulting α-siloxy ketone of the general formula

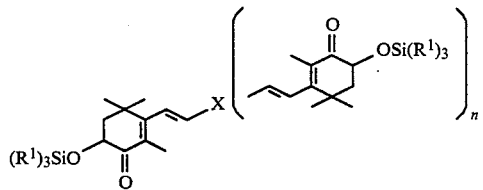

wherein n, X and $R^1$ have the above significances, to an α-hydroxy ketone of the general formula

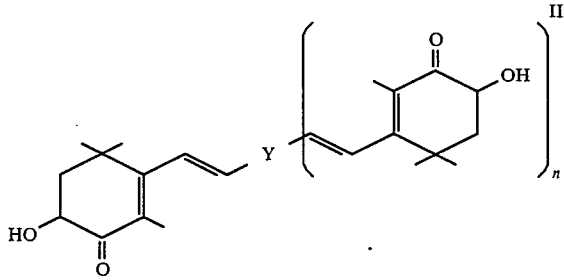

wherein n stands for the number 0 and Y stands for a group

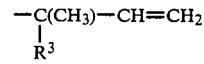

or n stands for the number 1 and Y stands for the 6,11-dimethylhexadeca-2,4,6,8,10,12,14-heptaene-2,15-diyl group, and $R^3$ represents the hydroxy group or an ether group.

The term "alkyl group" used herein embraces especially alkyl groups containing 1 to 20 carbon atoms such as methyl, ethyl, propyl, isopropyl, butyl, isobutyl, t-butyl, pentyl, decyl, octadecyl and the like. Preferred alkyl groups are those which contain 1 to 5 carbon atoms. Examples of trialkylsiloxy groups $-OSi(R^1)_3$ are triisopropylsiloxy, octadecyl-dimethylsiloxy and especially trimethylsiloxy and t-butyl-dimethylsiloxy.

The term "ether group" used herein embraces those ether groups which are usually introduced for the protection of a hydroxy group. Preferred ether groups are the alkoxy groups containing 1 to 5 carbon atoms and especially the methoxy group.

In formulae I–III above n preferably denotes the number 1 and X or Y preferably denotes the 6,11-dimethylhexadeca-2,4,6,8,10,12,14-heptaene-2,15-diyl group of the formula

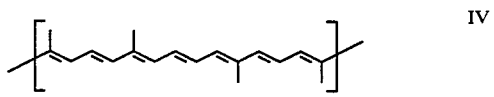

Further, in formulae I–III above n preferably denotes the number 0 and X or Y preferably denotes the group

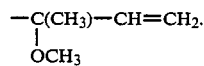

It has hitherto been possible to manufacture astaxanthin from canthaxanthin only in low yield via astacin and crustaxanthin [J. Chem. Soc. Chem. Commun. 49 (1967)]. The process provided by the present invention now provides simple access to astaxanthin from canthaxanthin or from intermediates in the synthesis of canthaxanthin.

The oxidation of a compound of formula I can be carried out under the conditions which are usually used in an epoxidation using a percarboxylic acid. In the present case there presumably takes place an epoxidation of the silylated enol group and opening of the epoxide ring with 1,4-migration of the silyl group. Examples of suitable percarboxylic acids are monoperphthalic acid, peracetic acid, perbenzoic acid, m-chloroperbenzoic acid, p-nitroperbenzoic acid, permaleic acid and the like. Peracetic acid, perbenzoic acid and especially monoperphthalic acid are preferred percarboxylic acids.

A partial hydrolysis of the reaction mixture can occur during the oxidation if large amounts of water or mineral acid are present. Consequently, a percarboxylic acid which is essentially free from water and mineral acid is preferably used. However, the oxidation can also be carried out using "technical" percarboxylic acids (e.g. 40% peracetic acid). In order to lessen the susceptibility to hydrolysis, in these cases there can conveniently be added a buffer salt, preferably a buffer having a pH-value of about 5–9, for example an acetate buffer, a carbonate buffer, a phosphate buffer (pH 6) and the like.

In order to achieve a conversion which is as complete as possible, the oxidation is conveniently carried out using an excess of percarboxylic acid. There are preferably used about 1.2–5 equivalents and especially about 1.6–3.0 equivalents of percarboxylic acid per silylated enol group. The oxidation is conveniently carried out in an inert organic solvent, for example an ether or a chlorinated or aromatic hydrocarbon such as diethyl ether, tetrahydrofuran, methylene chloride, toluene and the like. The ethers, especially diethyl ether, are preferred solvents. In order to achieve a high selectivity, the oxidation is preferably carried out in dilute solution (e.g. a 0.02–0.1M solution of the compound of formula I) and the contact time with the percarboxylic acid is kept short (e.g. about 10–60 minutes). Pressure and temperatures are not critical aspects in this oxidation; it is, however, preferably carried out at atmospheric pressure and a temperature of about −20° C. to about +30° C.

The hydrolysis of the compounds of formula II can be carried out according to methods known per se for the hydrolysis of silyl ethers; for example, by reaction with dilute mineral acids, aqueous organic acids, trialkylammonium fluoride and the like or by boiling in methanol, if desired with the addition of an acid (e.g. p-toluenesulphonic acid).

The compounds of formulae I and II above are novel and likewise form objects of the present invention.

The compounds of formula I can be prepared by converting a compound of the general formula

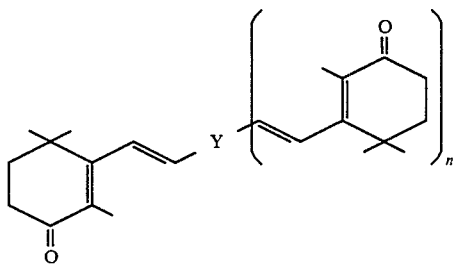

V wherein n and Y have the above significances, into a silyl-enol ether of formula I.

This process is novel and likewise forms an object of the present invention. It can be carried out according to methods known per se [e.g. Liebigs Ann. Chem. 1081, 1643, Tetrahedron Letters 22, 3455 (1981), Synthesis 1979, 35].

A preferred method for the silylation of a compound of formula V is the reaction of a compound of formula V with a trialkylhalosilane (e.g. trimethylchlorosilane or trimethyliodosilane) in the presence of an alkali metal dialkylamide (e.g. lithium diisopropylamide). The reaction is preferably carried out in an ether (e.g. tetrahydrofuran). Per carbonyl and hydroxy group in the compound of formula V there are conveniently used about 1.2–3.0 equivalents of silane and about 1.05–1.3 equivalents of dialkylamide, preferably about 2.0–2.4 equivalents of silane and about 1.2 equivalents of dialkylamide. Further, in many cases it has been found to be advantageous to provide the silane and the solvent and then to add the dialkylamide thereto. The temperature and pressure at which this reaction is carried out are not critical. However, in general, the reaction is carried out at atmospheric pressure and a temperature of about −40° C. to about +30° C., preferably at about −15° C.

A further method, which is especially suitable for the silylation of the compounds of formula V in which n stands for the number 0, is the reaction with a trialkylhalosilane (e.g. trimethylchlorosilane) in the presence of a trialkylamine (e.g. triethylamine). This reaction is preferably carried out in dimethylformamide under reflux.

A further preferred method is the reaction of a compound of formula V with a trifluoromethanesulphonic acid trialkylsilyl ester (e.g. the t-butyl-dimethylsilyl ester) in the presence of a trialkylamine (e.g. triethylamine). Methylene chloride is the preferred solvent. The pressure and temperature are not critical and, in general, the reaction is carried out at atmospheric pressure and a temperature between about −40° C. and room temperature, preferably about 0°–10° C.

A free hydroxy group which may be present in formula V is likewise silylated in these reactions, whereas a protected hydroxy group is not. By using an ether group the consumption of silylating agent can therefore be reduced. The introduction of the protecting group can be carried out according to methods known per se for the etherification of a hydroxy group. A subsequent cleavage of the protecting group is generally unnecessary, since it is eliminated in the further reaction of the compound of formula IIIB in accordance with Scheme 2.

According to the process provided by the invention astaxanthin is accessible in fewer steps from canthaxanthin or a known intermediate in the synthesis of canthaxanthin. Schemes 1 and 2 in which $R^1$, $R^2$ and $R^3$ have the above significances and X denotes chlorine or bromine illustrate a simple synthetic route and clearly show the correlation of the synthesis layout for n=0 or 1.

Scheme 1

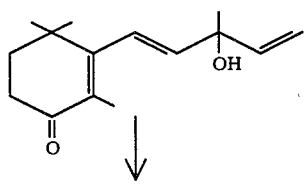

VB

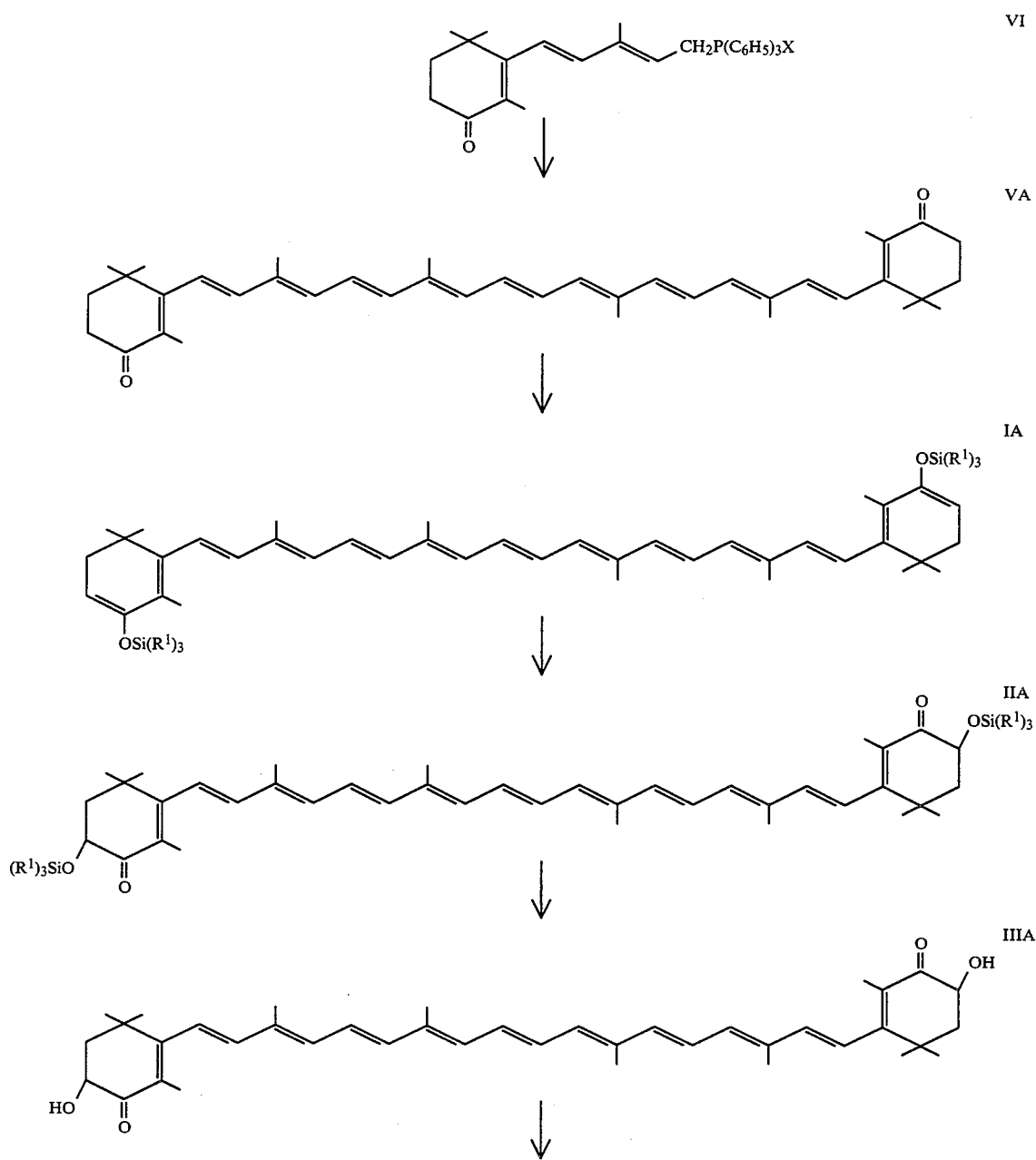
Scheme 2
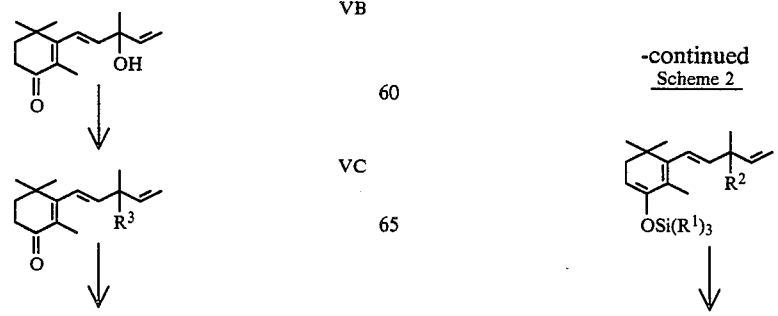

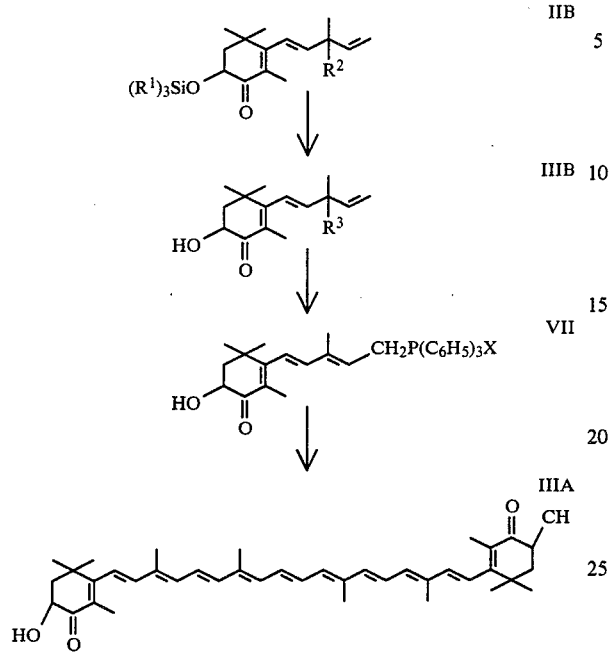

The compounds of formula VC, wherein $R^3$ represents an ether group, and the compounds of formula IIIB are novel and likewise form objects of the present invention.

The invention is also concerned with all novel compounds, processes and used as herein described.

The following Examples illustrate the invention:

EXAMPLE 1

(a) 14 ml of tetrahydrofuran and 1.64 ml of diisopropylamine were placed in a dry sulphonation flask equipped with a stirrer, thermometer, dropping funnel and argon gasification and cooled to −15° C. with an acetone/dry-ice bath. Subsequently, 9.5 ml of a solution of butyl lithium in hexane [content of butyl lithium 1.90M (18.1 mmol)] were added dropwise to the mixture from the dropping funnel in such a manner that the temperature could be held at −15° C. and the mixture was stirred at this temperature for 15 minutes.

(b) 2.83 g (5 mmol) of freshly recrystallized canthaxanthin and 3 ml (23.7 mmol) of trimethylchlorosilane in 100 ml of tetrahydrofuran were placed in a dry sulphonation flask equipped with a stirrer, thermometer, argon gasification and canula attachment and cooled to −15° C. to −20° C. by means of an acetone/dry-ice bath. The solution of lithium diisopropylamide prepared according to paragraph (a) was transferred completely into a gastight dosage syringe and added to the mixture with a dosage pump within 30 minutes at −15° C. After stirring for 5 minutes, the batch was rinsed into a separating funnel with 200 ml of diethyl ether and, with the addition of ice, extracted twice with in each case 200 ml of phosphate buffer solution (containing 6.8 g of potassium dihydrogen phosphate and 5.6 ml of 1N sodium hydroxide solution per liter of solution; pH 6) and then twice with in each case 200 ml of ice-water. In each washing operation the amount of tetrahydrofuran which dissolved in the aqueous phase was again added. The aqueous phases were back-washed once with 50 ml of diethyl ether. The organic phases were combined, dried over sodium sulphate, filtered and evaporated completely on a rotary evaporator at a bath temperature of 50° C. There were thus obtained 4.1 g of crude canthaxanthin bis(trimethylsilyl)-enol ether.

EXAMPLE 2

(a) The canthaxanthin bis(trimethylsilyl)-enol ether obtained according to Example 1 was rinsed with 100 ml of diethyl ether into a sulphonation flask equipped with a stirrer, thermometer, dropping funnel and argon gasification. Then, 1 g of sodium acetate and a spatula tip of Sequestrene were added and the suspension was cooled to −15° by means of an acetone/dry-ice bath. A solution of 2.9 g (16 mmol) of monoperphthalic acid in about 43 ml of diethyl ether (prepared by diluting the monoperphthalic acid solution described hereinafter with diethyl ether) was then added dropwise to the mixture from the dropping funnel within 15 minutes at −15° C., the temperature was then increased to 25° C. and the mixture was stirred for 45 minutes. The mixture was then rinsed into a separating funnel with 200 ml of tetrahydrofuran and extracted once with 50 ml of 0.5M sodium pyrosulphite solution, once with 50 ml of a semi-saturated sodium bicarbonate solution and once with 50 ml of a semi-saturated sodium chloride solution. The aqueous phases were back-washed once with 50 ml of diethyl ether. The organic phases were combined, dried over sodium sulphate, filtered and evaporated completely on a rotary evaporator at a bath temperature of 50° C. There were thus obtained 4.3 g of crude astaxanthin bis(trimethylsilyl)ether.

(b) The astaxanthin bis(trimethylsilyl)ether obtained was transferred with 80 ml of methanol into a round flask equipped with a reflux condenser, treated with a spatula tip of p-toluenesulphonic acid and heated at reflux for 30 minutes. The methanol was subsequently evaporated completely on a rotary evaporator at a bath temperature of 50° C. The entire crude product was dissolved in methylene chloride and analyzed by high pressure liquid chromatography. The yield based on canthaxanthin employed amounted to 67.5% of astaxanthin and 2.5% of adonirubin. In addition, 5% of unreacted canthaxanthin were found.

The monoperphthalic acid solution used above was prepared as follows:

300 ml of deionized water, 2.5 g of magnesium sulphate and 30 g of sodium hydroxide were placed in a sulphonation flask equipped with a stirrer, thermometer and dropping funnel and cooled to 5° C. with an ice-bath. 75 ml of 30% hydrogen peroxide were added dropwise to this mixture within about 2 minutes, the temperature rising to 10° C., and then a solution of 37.0 g of phthalic acid anhydride in 230 ml of tetrahydrofuran was added dropwise at 5°–10° C. within 15 minutes. After stirring for 10 minutes, the batch was poured into 600 ml of 20% sulphuric acid, the temperature rising from 0° C. to 10° C. The mixture was extracted three times with 250 ml of diethyl ether each time. The combined ether phases were back-washed twice with 200 ml of a 40% ammonium sulphate solution each time (the last wash water showed pH 4). Thse two phases were back-washed with 100 ml of diethyl ether. The combined ether phases were dried over sodium sulphate, filtered and concentrated to a volume of about 400 ml on a rotary evaporator at room temperature without a vacuum. The now about 10% monoperphthalic acid solution was poured into a four-necked flask and concentrated to a volume of about 130 ml by blowing in nitrogen while stirring. The solution obtained was about 30% (determined iodometrically). The chemical yield of monoperphthalic acid amounted to 88% based on phthalic acid anhydride.

EXAMPLE 3

A solution of 3.5 ml of diisopropylamine in 30 ml of tetrahydrofuran in a dry sulphonation flask equipped with a dropping funnel, thermometer, septum and argon gasification was treated dropwise (by means of a syringe) while stirring at −15° C. within 5 minutes with 12 ml of an about 2M solution of butyl lithium in hexane. The mixture was stirred at −15° for a further 15 minutes. A solution of 5.65 g of 96% canthaxanthin in 400 ml of tetrahydrofuran was subsequently added dropwise at −15° C. to −20° C. within about 20 minutes and the brown-violet suspension was stirred for 10 minutes. A solution of 4 ml of trimethylchlorosilane in 4 ml of tetrahydrofuran was then added dropwise to the mixture at −15° C., the cooling bath was removed and the red solution was stirred for a further 30 minutes. The mixture was poured on to 200 ml of diethyl ether and 200 ml of phosphate buffer solution pH 6 (as in Example 1) in a separating funnel and shaken out. The organic phase was extracted with 200 ml of phosphate buffer solution pH 6, subsequently washed three times with 200 ml of water each time, dried over sodium sulphate and concentrated to a volume of about 100 ml on a rotary evaporator at 30° C. This solution of canthaxanthin bis(trimethylsilyl)-enol ether was used directly for the subsequent reaction. By recrystallization of a sample from a diethyl ether/pentane/methanol mixture there was obtained canthaxanthin bis(trimethylsilyl)-enol ether in the form of violet needles; m.p. 168°–169° C.; Rf-values [diethyl ether/hexane, (2:3)]: canthaxanthin bis(trimethylsilyl)-enol ether about 0.75, canthaxanthin trimethylsilyl-enol ether about 0.54, canthazanthin about 0.30.

EXAMPLE 4

(a) The solution of canthaxanthin bis(trimethylsilyl)-enol ether obtained in Example 3 was treated while stirring in a sulphonation flask equipped with a dropping funnel, thermometer and argon gasification with 2 g of sodium acetate and 4 g of sodium sulphate and cooled to −15° C. A solution of 3.4 ml of about 40% peracetic acid (concentration 7.15M according to iodometric titration) in 34 ml of diethyl ether was added dropwise to this mixture within about 5 minutes, the cooling bath was then removed and the mixture was stirred for about 2 hours. The mixture was extracted in a separating funnel once with 100 ml of 0.5M ice-cold aqueous sodium pyrosulphite solution, twice with in each case 100 ml of semi-saturated aqueous sodium hydrogen carbonate solution and once with 100 ml of semi-saturated aqueous sodium chloride solution, dried over sodium sulphate and evaporated, there being obtained about 8 g of dark red solid crude product of astaxanthin bis(trimethylsilyl)ether; Rf-value about 0.67 [diethyl ether/hexane (2:1)]. By crystallization of a sample from methylene chloride/acetone the astaxanthin disilyl ether was obtained in the form of violet platelets; m.p. 196°–197° C.

(b) The crude product of the astaxanthin bis(trimethylsilyl)ether was taken up in 20 ml of methanol and boiled at reflux under argon for 4 hours. The mixture was left to cool to room temperature and was then cooled to −20° C., there being obtained a red-violet precipitation of 4.5 g of crude astaxanthin. Concentration of the mother liquor yielded about 3 g of solid red residue from which a further 0.4 g of crude astaxanthin was obtained by chromatography on silica gel with methylene chloride/diethyl ether (9:1) as the eluent and under an argon pressure of 0.2–0.4 bar. The resulting crude astaxanthin (4.9 g) was dissolved in 10 ml of methylene chloride and chromatographed on silica gel with methylene chloride/diethyl ether (9:1) as the eluent and an argon pressure of 0.2–0.4 bar. The uniform fractions were concentrated and recrystallized from methylene chloride/methanol, there being obtained 2.87 g of all-trans astaxanthin (purity about 90%); m.p. 216°–219° C.; yield 48% based on canthaxanthin.

EXAMPLE 5

A solution of 565 mg of canthaxanthin in 20 ml of methylene chloride was treated with 0.56 ml of triethylamine and cooled to about 3° C. with an ice-bath. 0.57 ml of t-butyl-dimethylsilyl trifluoromethanesulphonate were then added dropwise and the mixture was stirred without cooling for a further 30 minutes. The mixture was subsequently poured into a mixture of ice and saturated sodium chloride solution and extracted with diethyl ether. The ether phase was washed three times with water, dried over sodium sulphate and concentrated. The crude canthaxanthin bis(t-butyl-dimethylsilyl)-enol ether obtained can, without further purification, be processed directly in an analogous manner to Example 2 or Example 4. By complete evaporation of the crude enol ether there was obtained a dark red residue which, after recrystallization from diethyl ether/methanol, yielded in 70% yield canthaxanthin bis(t-butyl-dimethylsilyl)-enol ether in the form of fine violet needles; m.p. 166°–168° C.

EXAMPLE 6

A solution of 23.1 g of 96.5% 1-(3-oxo-2,6,6-trimethyl-1-cyclohexen-1-yl)-3-methyl-1,4-pentadien-3-ol in 85 ml of dimethylformamide in a four-necked flask equipped with a stirrer and reflux condenser was treated with 80 ml of triethylamine and 73 ml of trimethylchlorosilane. The mixture was heated to reflux (heating bath temperature 120° C.) for 2 hours while stirring and under a light argon stream. The mixture was subsequently cooled to about 0° C. with an ice-bath and treated while stirring with 400 ml of hexane and 200 ml of semi-saturated sodium hydrogen carbonate solution. The phases were separated and the aqueous phase was extracted with 200 ml of hexane. The combined organic phases were washed once with 100 ml of saturated sodium chloride solution, dried over sodium sulphate and concentrated at 40° C. in a rotary evaporator. Distillation of the resulting brown oil (39.5 g) at 102°–107° C./0.1 Torr gave 35.0 g of trimethyl[[1-methyl-3-[2,6,6-trimethyl-3-(trimethylsiloxy)-1,3-cyclohexadien-1-yl]-1-vinylallyl]oxy]silane as a pale yellowish oil; purity about 77%.

EXAMPLE 7

(a) 18.3 g of about 40% peracetic acid, 190 ml of absolute methylene chloride 3.8 g of anhydrous magnesium sulphate and 2.2 g of anhydrous sodium acetate were placed under argon in a four-necked flask equipped with a stirrer and cooled to −15° C. while stirring. To this suspension there was added dropwise within 10 minutes a solution of 35 g of 77% trimethyl[[1-methyl-3-[2,6,6-trimethyl-3-(trimethylsiloxy)-1,3-cyclohexadien-1-yl]-1-vinylallyl]oxy]silane (prepared according to Example 6) in 70 ml of methylene chloride. The ice-bath was removed and the mixture was stirred for a further 15 minutes, the temperature rising to 17° C. The mixture was treated while stirring with 38 g of anhydrous sodium carbonate and 38 g of sodium hydrogen carbonate, then stirred for a further 20 minutes and filtered (rinsing with 150 ml of methylene chloride). The filtrate (about 400 ml) containing trimethyl[[1-methyl-3-[2,6,6-trimethyl-3-oxo-4-(trimethylsiloxy)-1-cyclohexen-1-yl]-1-vinylallyl]oxy]silane was processed directly.

(b) The filtrate obtained was treated while stirring vigorously at room temperature with 40 ml of triethylammonium fluoride and then stirred for a further 20 hours. The solution was washed successively with 100 ml of semi-saturated sodium chloride solution, 100 ml of semi-saturated aqueous sodium pyrosulphite solution and with 100 ml of semi-saturated sodium chloride solution, dried over sodium sulphate and concentrated in a rotary evaporator at 40° C. (bath temperature). There were thus obtained 25.3 g of 1-(4-hydroxy-3-oxo-2,6,6-trimethyl-1-cyclohexen-1-yl)-3-methyl-1,4-pentadien-3-ol as a yellowish oil; purity 79.8% according to gas chromatography.

(c) The 1-(4-hydroxy-3-oxo-2,6,6-trimethyl-1-cyclohexen-1-yl)-3-methyl-1,4-pentadien-3-ol obtained was converted in 250 ml of methylene chloride with 30 ml of 63% hydrogen bromide solution into the bromide and the bromide was subsequently converted with 26.2 g of triphenylphosphine into the phosphonium bromide. There were thus obtained 45.3 g of crude [(4E)-5-(4-hydroxy-2,6,6-trimethyl-3-oxo-1-cyclohexen-1-yl)-3-methyl-2,4-pentadienyl]-triphenylphosphonium bromide; m.p. 157°–163° C. After recrystallization from ethyl acetate/methylene chloride 2:1 at 0° C., there were obtained 32.4 g of 89.9% trans product; m.p. 181°–182° C. After two further recrystallizations from ethyl acetate/methylene chloride, the purity was 96%; m.p. 186°–187° C.

EXAMPLE 8

22.2 g of diisopropylamine were dissolved in 330 ml of absolute tetrahydrofuran in a four-necked flask equipped with a stirrer and cooled to −15° C. under argon. To this solution there were added dropwise while stirring 106 ml of an about 2M solution of butyl lithium in hexane and after 10 minutes a solution of 23.2 g of 97% 1-(3-oxo-2,6,6-trimethyl-1-cyclohexen-1-yl)-3-methyl-1,4-pentadien-3-ol in 40 ml of absolute tetrahydrofuran. 48 ml of trimethylchlorosilane were subsequently added dropwise thereto in such a manner that the temperature could be held at −15° C. The mixture again became homogeneous. After the addition, the cooling bath was removed and the mixture was allowed to warm to room temperature. The mixture was transferred into a 2 l flask (rinsing with pentane) and the solvent was removed on a rotary evaporator in vacuo at about 40° C. (bath temperature). The residue was taken up in about 250 ml of pentane, the suspension obtained was filtered and the filter residue was rinsed several times with pentane (total 250 ml). The filtrate was evaporated in a rotary evaporator and the crude product (43.3 g) was distilled at 110° C./0.01 Torr. There were thus obtained 37.2 g of trimethyl[[1-methyl-3-[2,6,6-trimethyl-3-(trimethylsiloxy)-1,3-cyclohexadien-1-yl]-1-vinylallyl]oxy]silane in a purity of 98% as a pale yellowish oil.

EXAMPLE 9

(a) 37.2 g of trimethyl[[1-methyl-3-[2,6,6-trimethyl-3-(trimethylsiloxy)-1,3-cyclohexadien-1-yl]-1-vinylallyl]oxy]silane (purity 98%) were dissolved in 250 ml of absolute diethyl ether and treated under argon and while stirring well with 24.7 g of sodium hydrogen carbonate, 31.2 g of sodium carbonate and 24.4 g of sodium acetate. The mixture was stirred at −5° C. for 10 minutes and then treated within 20 minutes with 326 ml of a 0.9N solution of monoperphthalic acid in diethyl ether. The mixture was poured into 100 ml of saturated sodium hydrogen carbonate solution and extracted with a mixture of 500 ml of water and 500 ml of diethyl ether. The organic phase was washed once with 200 ml of semi-saturated sodium pyrosulphite solution and twice with 100 ml of sodium chloride solution each time and then evaporated. The evaporation residue (41.2 g) of trimethyl[[1-methyl-3-[2,6,6-trimethyl-3-oxo-4-(trimethylsiloxy)-1-cyclohexen-1-yl]-1-vinylallyl]oxy]silane was processed directly.

(b) The evaporation residue was dissolved in 200 ml of methylene chloride, then treated with 40 ml of triethylammonium fluoride solution and stirred at room temperature for 4 hours. The mixture was subsequently poured into 100 ml of semi-saturated sodium hydrogen carbonate solution and the organic phase was then separated and evaporated. There were thus obtained 28.0 g of evaporation residue of 1-(4-hydroxy-3-oxo-2,6,6-trimethyl-1-cyclohexen-1-yl)-3-methyl-1,4-pentadien-3-ol as an oil which was processed directly.

(c) The resulting oil was taken up in 250 ml of absolute methylene chloride under argon at 0° C. and treated within 10 minutes with 30 ml of 63% hydrogen bromide solution. The mixture was taken up in about 0.5 l of ethyl acetate, washed once with saturated sodium chloride solution and once with saturated sodium hydrogen carbonate solution, dried over sodium sulphate and concentrated to about 300 ml in a rotary evaporator at 30° C. (bath temperature). The thus-obtained bromide solution was added dropwise to a solution of 26.2 g f triphenylphosphine in 100 ml of absolute ethyl acetate and stirred overnight at room temperature. After filtration, there were obtained 49.0 g of crude [5-(4-hydroxy-2,6,6-trimethyl-3-oxo-1-cyclohexen-1-yl)-3-methyl-2,4-pentadienyl]-triphenylphosphonium bromide (content according to high pressure liquid chromatography: 77.2% of 2E-isomer and 12.1% of 2Z-isomer); m.p. 162°–164° C. Recrystallization from 200 ml of methylene chloride and 400 ml of ethyl acetate gave 43.2 g of phosphonium salt (content: 84.5% of 2E-isomer and 10% of 2Z-isomer); m.p. 178°–180° C.

EXAMPLE 10

(a) 2.34 g of 1-(3-oxo-2,6,6-trimethyl-1-cyclohexen-1-yl)-3-methyl-1,4-pentadien-3-ol were dissolved in 15 ml of hexane and 5 ml of diethyl ether, treated with 2 drops of tricaprylm thylammonium chloride and 4.54 ml of aqueous potassium hydroxide solution (prepared from 70 g of powdered potassium hydroxide and 50 ml of water) and stirred well. 1.98 g of dimethyl sulphate were subsequently added to the mixture and the course of the reaction was followed by gas chromatography. After stirring at room temperature for 4 hours (product/educt ratio 99.7:0.3), the mixture was poured on to ice. The organic phase was separated, washed neutral with water, dried over sodium sulphate and concentrated under a water-jet vacuum. There were obtained 2.47 g of 1-(3-oxo-2,6,6-trimethyl-1-cyclohexen-1-yl)-3-methoxy-3-methyl-1,4-pentadiene as a yellow oil.

(b) A solution of 19.5 g of diisopropylamine in 300 ml of absolute tetrahydrofuran was cooled to −20° C., treated dropwise with 126 ml of a 1.6M solution of butyl lithium in hexane and stirred at −20° C. for a further 20 minutes. The mixture was then treated dropwise with a solution of 40.0 g of 1-(3-oxo-2,6,6-trimethyl-1-cyclohexen-1-yl)-3-methoxy-3-methyl-1,4-pentadiene in 50 ml of absolute tetrahydrofuran and the resulting mixture was stirred at 0° C. for a further 1 hour. After cooling to −20° C. and the rapid dropwise addition of 21 g of trimethylchlorosilane, the mixture was stirred at 0° C. for 15 minutes (according to gas chromatography 96.5% of the educt were converted into the desired product at this point in time). The mixture was treated dropwise with 80 ml of saturated sodium chloride solution and then extracted with diethyl ether. The organic phase was washed three times with saturated sodium chloride solution, dried over sodium sulphate and concentrated in a water-jet vacuum. There were obtained 51.0 g of 1-[2,6,6-trimethyl-3-(trimethylsiloxy)-1,3-cyclohexadien-1-yl]-3-methoxy-3-methyl-1,4-pentadiene (purity 96.36%).

EXAMPLE 11

(a) A mixture of 32.0 g of 1-[2,6,6-trimethyl-3-(trimethylsiloxy)-1,3-cyclohexadien-1-yl]-3-methoxy-3-methyl-1,4-pentadiene, 10.0 g of sodium hydrogen carbonate, 10.0 g of magnesium sulphate trihydrate and 500 ml of diethyl ether was stirred well at 2°–5° C., then treated dropwise with 26.45 g of 40% peracetic acid and left to warm to room temperature. The mixture was subsequently cooled to 0° C., treated dropwise with 90 ml of a mixture of methanol and 1N hydrochloric acid (vol. 1:1) and extracted with diethyl ether. The organic phase was washed twice with cold semi-concentrated sodium pyrosulphite solution, once with ice-water, twice with ice-water to which had been added a small amount of saturated sodium hydrogen carbonate solution and a further twice with ice-water. After drying over sodium sulphate and concentration under a water-jet vacuum at 35° C., there were obtained 26.4 g of crude 1-(4-hydroxy-3-oxo-2,6,6-trimethyl-1-cyclohexen-1-yl)-3-methoxy-3-methyl-1,4-pentadiene (purity 91.5%) which still contained 7.07% of 1-(3-oxo-2,6,6-trimethyl-1-cyclohexen-1-yl)-3-methoxy-3-methyl-1,4-pentadiene.

(b) A solution of 58.0 g of crude 91.55% 1-(4-hydroxy-3-oxo-2,6,6-trimethyl-1-cyclohexen-1-yl)-3-methoxy-3-methyl-1,4-pentadiene in 400 ml of methylene chloride was stirred at −20° C., rapidly treated dropwise with 38.5 g of 63% aqueous hydrogen bromide solution and subsequently stirred at −15° C. for a further 10 minutes. The mixture was extracted with cold ethyl acetate. The extract was washed with cold 25% aqueous sodium bromide solution and a small amount of saturated sodium hydrogen carbonate solution and then concentrated to a volume of about 70–80 ml under a water-jet vacuum at room temperature. The solution obtained was added to a solution of 52.4 g of triphenylphosphine in 200 ml of ethyl acetate and the mixture was stirred at room temperature for about 3–4 hours. After crystallization of the product, the mixture was stirred at 5° C. for a further 15 hours, then suction filtered and the filter material was dried at 35° C. under a water-jet vacuum. The resulting crude phosphonium salt (95.3 g) was recrystallized from 200 ml of methylene chloride and 400 ml of ethyl acetate. There were thus obtained 80.35 g of [(4E)-5-(4-hydroxy-2,6,6-trimethyl-3-oxo-1-cyclohexen-1-yl)-3-methyl-2,4-pentadienyl]-triphenylphosphonium bromide (containing 83.36% of 2E-isomer and 13.55% of 2Z-isomer); m.p. 179°–182° C.

We claim:

1. Compounds of the general formula

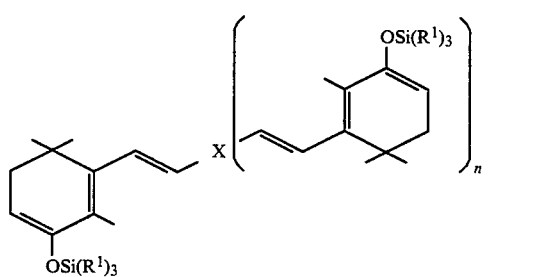

I wherein n stands for the number 0 and X stands for a group

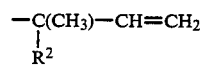

or n stands for the number 1 and X stands for the 6,11-dimethylhexadeca-2,4,6,8,10,12,14-heptaene-2,15-diyl group, the symbols $R^1$ have the same or different significances and denote alkyl groups, and the symbol $R^2$ represents a trialkylsiloxy group $—OSi(R^1)_3$ or an ether group.

2. Compounds of the general formula

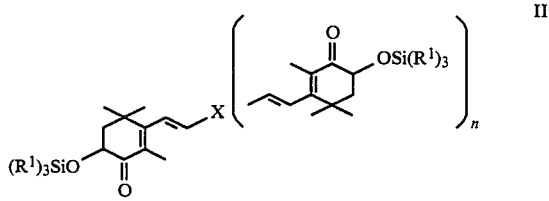

II wherein n stands for the number 0 and X stands for a group

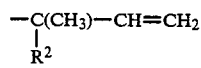

or n stands for the number 1 and X stands for the 6,11-dimethylhexadeca-2,4,6,8,10,12,14-heptaene-2,15-diyl group, the symbols $R^1$ have the same or different significances and denote alkyl groups, and the symbol $R^2$ represents a trialkylsiloxy group $—OSi(R^1)_3$ or an ether group.

* * * * *